United States Patent
Hadba et al.

(10) Patent No.: US 8,044,234 B2
(45) Date of Patent: Oct. 25, 2011

(54) BIOABSORBABLE SURGICAL COMPOSITION

(75) Inventors: Ahmad R. Hadba, Wallingford, CT (US); Walter Skalla, Old Lyme, CT (US); Nadya Belcheva, Middletown, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1358 days.

(21) Appl. No.: 11/123,690

(22) Filed: May 5, 2005

(65) Prior Publication Data
US 2006/0253094 A1    Nov. 9, 2006

(51) Int. Cl.
C07C 273/00    (2006.01)
A61F 13/15    (2006.01)
A61K 47/30    (2006.01)

(52) U.S. Cl. ............ 560/335; 514/772.1; 560/330; 604/389

(58) Field of Classification Search .............. None
See application file for complete search history.

(56) References Cited

U.S. PATENT DOCUMENTS

| | | |
|---|---|---|
| 3,773,595 A | 11/1973 | Burba et al. |
| 4,057,535 A | 11/1977 | Lipatova et al. |
| 4,061,662 A | 12/1977 | Marans et al. |
| 4,169,175 A | 9/1979 | Marans et al. |
| 4,321,350 A | 3/1982 | Lehmann |
| 4,323,491 A | 4/1982 | Veselovsky et al. |
| 4,404,296 A | 9/1983 | Schapel |
| 4,425,472 A | 1/1984 | Howard et al. |
| 4,451,627 A | 5/1984 | Frisch, Jr. et al. |
| 4,477,604 A | 10/1984 | Oechsle, III |
| 4,547,561 A | 10/1985 | Wegner |
| 4,654,409 A | 3/1987 | Shirai et al. |
| 4,740,534 A | 4/1988 | Matsuda et al. |
| 4,762,899 A | 8/1988 | Shikinami |
| 4,804,691 A | 2/1989 | English et al. |
| 4,829,099 A | 5/1989 | Fuller et al. |
| 4,883,837 A | 11/1989 | Zabrocki |
| 4,994,208 A | 2/1991 | McBain et al. |
| 5,166,300 A | 11/1992 | Rumon et al. |
| 5,169,720 A | 12/1992 | Braatz et al. |
| 5,175,228 A | 12/1992 | Wang et al. |
| 5,346,981 A | 9/1994 | Sarpeshkar et al. |
| 5,374,704 A | 12/1994 | Muller et al. |
| 5,462,536 A | 10/1995 | Braatz et al. |
| 5,574,104 A | 11/1996 | Kolycheck et al. |
| 5,717,030 A | 2/1998 | Dunn et al. |
| 5,780,573 A | 7/1998 | Iwata et al. |
| 5,795,633 A | 8/1998 | Yokoyama et al. |

(Continued)

FOREIGN PATENT DOCUMENTS
EP    0 077 192 A2    4/1983
(Continued)

OTHER PUBLICATIONS
U.S. Appl. No. 11/635,294, filed Dec. 2006, Hadba et al.*
(Continued)

*Primary Examiner* — Frederick Krass
*Assistant Examiner* — Brian Gulledge (57) ABSTRACT

Compounds are provided which can form bioabsorbable compositions useful as adhesives or sealants for medical/surgical applications. In embodiments, suitable compositions may possess various functional groups, including groups derived from multifunctional compounds, aliphatic or aromatic groups, groups derived from aliphatic diacids, groups derived from a dihydroxy compound, and combinations thereof. Methods for forming these compositions, as well as uses thereof, are also provided.

2 Claims, 1 Drawing Sheet

U.S. PATENT DOCUMENTS

| | | | |
|---|---|---|---|
| 5,869,566 | A | 2/1999 | Thomas |
| 5,900,473 | A | 5/1999 | Acevedo et al. |
| 5,912,193 | A | 6/1999 | Iwata et al. |
| 5,990,237 | A | 11/1999 | Bentley et al. |
| 6,071,530 | A | 6/2000 | Polson |
| 6,154,089 | A | 11/2000 | Rombach |
| 6,162,241 | A | 12/2000 | Coury et al. |
| 6,197,915 | B1 | 3/2001 | Yamana et al. |
| 6,261,544 | B1 | 7/2001 | Coury et al. |
| 6,297,349 | B1 | 10/2001 | Goldberg et al. |
| 6,376,742 | B1 * | 4/2002 | Zdrahala et al. ........... 623/11.11 |
| 6,395,112 | B1 | 5/2002 | Sitzmann et al. |
| 6,395,823 | B1 | 5/2002 | Brink et al. |
| 6,495,127 | B1 | 12/2002 | Wallace et al. |
| 6,555,645 | B1 | 4/2003 | Ikeda et al. |
| 6,565,969 | B1 | 5/2003 | Lamon et al. |
| 6,566,406 | B1 * | 5/2003 | Pathak et al. ............. 514/772.1 |
| 6,576,702 | B2 | 6/2003 | Anderle et al. |
| 6,579,952 | B1 | 6/2003 | Niki et al. |
| 6,582,713 | B2 | 6/2003 | Newell et al. |
| 6,605,666 | B1 | 8/2003 | Scholz et al. |
| 6,824,703 | B2 | 11/2004 | Lawrey et al. |
| 2002/0028875 | A1 | 3/2002 | Anderle et al. |
| 2003/0032734 | A1 | 2/2003 | Roby |
| 2003/0176615 | A1 | 9/2003 | Lawrey et al. |
| 2003/0195293 | A1 | 10/2003 | Lubnin et al. |
| 2004/0019178 | A1 | 1/2004 | Gross et al. |
| 2004/0023842 | A1 | 2/2004 | Pathak et al. |
| 2004/0068078 | A1 | 4/2004 | Milbocker |
| 2004/0092695 | A1 | 5/2004 | Hu et al. |
| 2004/0198901 | A1 | 10/2004 | Graham et al. |
| 2004/0198944 | A1 | 10/2004 | Meltzer et al. |
| 2004/0242831 | A1 | 12/2004 | Tian et al. |
| 2004/0259968 | A1 | 12/2004 | Krebs |
| 2005/0004661 | A1 | 1/2005 | Lewis et al. |
| 2005/0069573 | A1 | 3/2005 | Cohn et al. |
| 2005/0070913 | A1 | 3/2005 | Milbocker et al. |
| 2005/0129733 | A1 | 6/2005 | Milbocker et al. |
| 2005/0131192 | A1 | 6/2005 | Matsuda et al. |
| 2005/0142162 | A1 | 6/2005 | Hunter et al. |
| 2005/0147647 | A1 | 7/2005 | Glauser et al. |
| 2005/0154148 | A1 | 7/2005 | Nakamichi et al. |
| 2005/0266086 | A1 | 12/2005 | Sawhney |

FOREIGN PATENT DOCUMENTS

| | | | |
|---|---|---|---|
| EP | 0482467 | * | 10/1991 |
| EP | 0 482 467 | | 4/1992 |
| EP | 0 488 629 | | 6/1992 |
| EP | 0 301 516 | | 9/1992 |
| EP | 1 391 205 | A1 | 2/2005 |
| EP | 1 719 530 | A | 11/2006 |
| EP | 1857489 | A1 | 11/2007 |
| GB | 985 144 | | 3/1965 |
| JP | 6263850 | | 9/1994 |
| JP | 2002060341 | | 2/2002 |
| WO | WO0043050 | | 7/2000 |
| WO | WO 01/00246 | A | 1/2001 |
| WO | WO 01/16210 | A | 3/2001 |
| WO | WO 2002/056790 | A2 | 7/2002 |
| WO | WO03011173 | | 2/2003 |
| WO | WO2004/039323 | | 5/2004 |
| WO | WO2004039857 | | 5/2004 |
| WO | WO2004041890 | | 5/2004 |
| WO | WO 2005/032461 | A2 | 4/2005 |
| WO | WO 2005/100429 | A1 | 10/2005 |
| WO | WO 2006/010278 | A1 | 2/2006 |
| WO | WO 2006/084911 | A2 | 8/2006 |
| WO | WO 2006/107957 | A2 | 10/2006 |
| WO | WO 2006/128742 | A2 | 12/2006 |
| WO | WO 2006/128918 | A1 | 12/2006 |
| WO | WO 2007/001448 | A2 | 1/2007 |
| WO | WO 2007/067623 | A | 6/2007 |
| WO | WO 2008/047100 | A1 | 4/2008 |

OTHER PUBLICATIONS

U.S. Appl. No. 11/635,365, filed Dec. 2006, Hadba et al.*
European Search Report (EP 06 00 9170).
Margolin A L et al.: "Stereoselective Oligomerizations Catalyzed by Lipases In Organic Olvents"; Tetrahedron Letters, vol. 28, No. 15, 1987, pp. 1607-1610.
Okumura S. et al: "Synthesis of Ester Oligomer by Aspergillus-Niger Lipase" Agricultural and Biological Chemistry, vol. 48, No. 11, 1984, pp. 2805-2808.
Lumann N R et al.: "The Convergent Synthesis of Poly(glycerol-succininc acid) Dendritic Macromolecules" Chemistry—A European Journal, VCH Publishers, US, vol. 9, 2003, pp. 5618-5626.
Database WPI, Section Ch, Week 199442 Derwent Publications Ltd., London, GB; Class A23, AN 1994-338349.
Nivasu V M et al: "In Situ Polymerizable Polyethyleneglycol Containing Polyesterpolyol Acrylates for Tissue Sealant Applications"; Biomaterials 2004 United Kingdom, vol. 25, No. 16, 2004, pp. 3283-3291.
Moon S-Y et al.: "Polyurethane/Montorillonite Nanocomposites Prepared From Crystalline Polyols, Using 1, 4-Butanediol and Organoclay Hybrid as Chain Extenders" European Polymer Journal, Pergamon Press Ltd. Oxford, GB,; vol. 40, No. 8, Aug. 2004; pp. 1615-1621.
M.J. Song, D. S. Lee, J.H. Ahn, D.J. Kim, S.C. Kim: "Thermosensitive Sol-Gel Transition Behaviors of Poly(ethylene oxide)/ Aliphatic Polyester/Poly(ethylene Oxide) Aqueous Solutions"; Journal of Polymer Science Part A: Polymer Chemistry, vol. 42, No. 3. ; Feb. 1, 2004 pp. 772-784.
Mei Xuan Xu et al: "Synthesis and Properties of Unsaturated Polyester Diol-Polyurethanehybrid Polymer Network" Journal of Applied Polymer Science, John Wiley and Sons Inc. New York, US, vol. 54, No. 11, Dec. 12, 1994, pp. 1659-1663.
Oprea S. et al.: "Poly(urethane-methacrylate)s. Synthesis and Characterization"; Polymer, Elsevier Science Publishers B.V., GB, vol. 42, No. 17, Aug. 2001, pp. 7257-7266.
International Search Report from PCT/US06/47013 dated Oct. 3, 2007.
International Search Report from PCT/US06/46558 dated Nov. 9, 2007.
International Search Report from PCT/US06/46552 dated Nov. 15, 2007.
International Search Report from PCT/US06/47023 dated Nov. 21, 2007.
International Search Report from Application EP 07 00 1213 dated Sep. 6, 2007.
International Search Report from Application EP 03 77 9244 dated Sep. 26, 2007.
International Search Report from Application PCT/US2006/46553 dated Oct. 31, 2007.
International Search Report from Application PCT/US2006/46554 dated Oct. 31, 2007.
International Search Report from Application No. PCT/US08/60971 dated Jul. 18, 2008.
European Search Report for Appln. No. EP 08 25 3647 completed Mar. 6, 2009.
European Search Report for Appln. No. EP 08 25 1790.5 completed Jun. 19, 2009.
International Search Report from European Application No. EP 06 84 4894 date of completion Jun. 9, 2010.
International Search Report from European Application No. EP 06 84 4890 date of completion Jun. 4, 2010.

* cited by examiner

Figure 1

BIOABSORBABLE SURGICAL COMPOSITION

TECHNICAL FIELD

The present disclosure relates to compounds suitable for use in forming bioabsorbable compositions which, in turn, are capable of being used as surgical adhesives or sealants.

RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed.

It would be desirable to provide a fully synthetic biological adhesive or sealant that is flexible, biocompatible and highly consistent in its properties. It would also be desirable if the adhesive or sealant was of sufficiently low viscosity to be applied to the desired field.

SUMMARY

The present disclosure provides compounds of the formula:

HO—(R-A)$_n$-R—OH wherein A is a group derived from an aliphatic diacid; R can be the same or different at each occurrence and is a group derived from a dihydroxy compound having a molecular weight less than 1,000; and n is 2 to 10. Such compounds are not solids, but rather are flowable.

The present disclosure also provides compounds of the formula:

OCN—X—HNCOO—(R-A)$_n$-ROOCNH—X—NCO wherein X is an aliphatic or aromatic group; A is a group derived from an aliphatic diacid; R can be the same or different at each occurrence and is a group derived from a dihydroxy compound; and n is 1 to 10.

The present disclosure also provides compounds of the formula:

Z—(OOCNH—X—NHCOO—(R-A)$_n$R—OOCNH—
    X—NCO)$_m$ wherein Z is a group derived from a multifunctional compound; X is an aliphatic or aromatic group; A is a group derived from an aliphatic diacid; R can be the same or different at each occurrence and is a group derived from a dihydroxy compound; n is 1 to 10; and m is 2 to 6.

Compositions containing the aforementioned compounds are also described herein. The compounds and compositions are useful, for example, as an adhesive or sealant, and can be applied to tissue or used to seal an opening in tissue to prevent leakage of air or bodily fluid or used to close a wound or used to secure a medical device or prosthesis to tissue.

DETAILED DESCRIPTION

The present disclosure relates to compounds suitable for forming a bioabsorbable composition which may be used as a tissue adhesive or sealant.

The compositions of the present disclosure contain a component that includes an aliphatic diacid linking two dihydroxy compounds (sometimes referred to herein as an "aliphatic polyester macromer"). Up to ten repeats of the aliphatic polyester macromer may be present. The present compounds are not solid at the temperatures encountered in use, but rather are flowable. Flowable materials have a measurable viscosity. For example, the present compounds may have a viscosity of about 1,000 to about 300,000 centipoise ("Cp") at temperatures of about 0° C. to about 40° C.

Suitable aliphatic diacids which may be utilized in forming the compounds include, for example, aliphatic diacids having from about 2 to about 8 carbon atoms suitable diacids include, but are not limited to sebacic acid, azelaic acid, suberic acid, pimelic acid, adipic acid, glutaric acid, succinic acid, malonic acid, oxalic acid and combinations thereof.

Suitable dihydroxy compounds which may be utilized include, for example, polyols including polyalkylene oxides, polyvinyl alcohols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO).

In one embodiment, a polyethylene glycol ("PEG") may be utilized as the dihydroxy compound. It may be desirable to utilize a PEG with a molecular weight ranging from about 200 to about 1000, typically from about 400 to about 900. Suitable PEGs are commercially available from a veracity of sources under the designations PEG 200, PEG 400, PEG 600 and PEG 900.

Any method may be used to form the aliphatic polyester macromer. In some embodiments, the aliphatic polyester macromer may be formed by combining adipoyl chloride with a PEG such as PEG 600 and pyridine in a suitable solvent, such as tetrahydrofuran (THF). The solution may be held at a suitable temperature, from about −70° C. to about 25° C., for a period of time ranging from about 4 hours to about 18 hours, after which the reaction mixture is filtered to remove the precipitated pyridine hydrochloride by-product and the resulting aliphatic polyester macromer, here a PEG/adipate compound, may be precipitated from the solution by the addition of ether or petroleum ether, and collected by suitable means which can include filtration. Other methods suitable for making the present compounds will be apparent to those skilled in the art.

Typically, the resulting aliphatic polyester macromer is of the following formula:

HO—(R-A)$_n$-R—OH wherein A is a group derived from an aliphatic diacid; R can be the same or different at each occurrence and is a group derived from a dihydroxy compound; and n is 1 to 10. In some useful embodiments, the A group can be derived from adipic acid and R can be derived from a polyethylene glycol having a molecular weight of less then 1,000. The molecular weight and viscosity of these compounds will depend on a number of factors such as the particular diacid used, the particular dihydroxy compound used and the number of repeat units present. Generally, the viscosity of these compounds may be from about 300 to about 10,000 Cp at 25° C. and a shear rate of 20.25 s$^{-1}$.

These compounds are useful for a number of applications. For example, they may be used to produce compounds capable of cross-linking to form a gel matrix that serves as an excellent tissue adhesive or sealant.

For adhesive or sealant applications, it may be desirable to endcap the above aliphatic polyester macromer to provide a reactive end group. Suitable reactive end groups include amine reactive end groups, for example, isocyanate groups, isothiocyanates, diimidazoles, imidoesters, hydroxysuccinimide esters, and aldehydes. Of particular interest are the isocyanate groups. Methods for endcapping the aliphatic polyester macromer to provide a reactive end group are within the purview of those skilled in the art.

For example, the aliphatic polyester macromer may be reacted with an aliphatic or aromatic diisocyanate to produce a diisocyanate-functional compound. Suitable isocyanates for endcapping the aliphatic polyester macromer include aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science.

Methods for endcapping the aliphatic polyester macromer with a diisocyanate are within the purview of those skilled in the art. For example, the aliphatic polyester macromer may be combined with a suitable diisocyanate, such as toluene diisocyanate, and heated to a suitable temperature ranging from about 55° C. to about 75° C., typically about 65° C. The resulting diisocyanate-functional compound may then be purified by hot extraction with petroleum ether.

The diisocyanate-functional compounds of the present disclosure may be of the following formula:

OCN—X—HNCOO—(R-A)$_n$-R—OOCNH—X—NCO wherein X is an aliphatic or aromatic group; A is a group derived from an aliphatic diacid; R can be the same or different at each occurrence and is a group derived from a dihydroxy compound; and n is 1 to 10. In some embodiments, X may derived from toluene, hexamethylene, tetramethylene, lysine, ethylated lysine isophorone, xylene, diphenylmethane, diphenyldimethylmethane, dibenzyl diisocyanate, oxybis(phenylisocyanate), tetramethylxylylene or optionally mixtures thereof or combinations thereof. The NCO content of the diisocyanate-functional compound can vary from about 3% to about 6%, typically from about 3.5% to about 5%. The viscosity of these diisocyanate-functional compounds will depend on a number of factors such as the particular diisocyanate used, the particular diacid used, the particular dihydroxy compound used and the number of repeat units present. Generally, the viscosity of these compounds may be from about 1,500 to about 50,000 Cp.

It should be understood that more than one different aliphatic polyester macromer can be endcapped in a single reaction. For example, aliphatic polyester macromer of the above-mentioned formula wherein n is 3 can be prepared and combined with aliphatic polyester macromer of the above-mentioned formula wherein n is 5 that had been separately prepared. The mixture of aliphatic polyester macromers can then be endcapped to provide a reactive group in a single reaction. The resulting product will be a mixture of diisocyanate-functional compounds of the formula shown above.

In another aspect of the present disclosure, the functionalized polyester macromer may be further reacted with a multifunctional compound which acts as a branching agent. Suitable branching agents include, for example, polyfunctional acids, anhydrides, alcohols, and mixtures thereof. In some embodiments, the multifunctional compound may be a polyol having 3 to 6 hydroxyl groups, a polycarboxylic acid having 3 to 6 carboxyl groups or a hydroxy acid having a total of 3 to 6 hydroxyl and carboxyl groups.

Representative polyols that may be utilized as the multifunctional compound include glycerol, trimethylol propane, 1,2,4-butanetriol, pentaerythritol, 1,2,6-hexanetriol, sorbitol, 1,1,4,4-tetrakis(hydroxymethyl)cyclohexane, tris(2-hydroxyethyl)isocyanurate, polycaprolactone triol, polylactide triol, polyglycolic acid triol, polydioxanone triol, dipentaerythritol or optionally mixtures thereof. Other multifunctional compounds which may be utilized include triols derived by condensing alkylene oxides having 2 to 3 carbons, such as ethylene oxide and propylene oxide, with polyol initiators. Such multifunctional compounds typically have higher molecular weights ranging from about 400 to about 3000.

Representative polycarboxylic acids that may be used as the multifunctional compound include hemimellitic acid, trimellitic acid, trimesic acid, pyromellitic acid, benzene tetracarboxylic acid, benzophenone tetracarboxylic acid, 1,1,2,2-ethanetetracarboxylic acid, 1,1,2-ethanetricarboxylic acid, 1,3,5-pentanetricarboxylic acid, and 1,2,3,4-cyclopentane-tetra-carboxylic acid.

Representative hydroxy acids suitable as the multifunctional compound include malic acid, citric acid, tartaric acid, 3-hydroxyglutaric acid, mucic acid, trihydroxyglutaric acid, and 4-(beta-hydroxyethyl)phthalic acid. Such hydroxy acids contain a combination of 3 or more hydroxyl and carboxyl groups.

In some embodiments, the multifunctional compound may include at least one bioabsorbable group to alter the degradation profile of the resulting branched, functionalized compound. Bioabsorbable groups which may be combined with the multifunctional compound include, for example groups derived from glycolide, glycolic acid, lactide, lactic acid, caprolactone, dioxanone, trimethylene carbonate, and combinations thereof. For example, in one embodiment the multifunctional compound may include trimethylol propane in combination with dioxanone and glycolide. Methods for adding bioabsorbable groups to a multifunctional compound are known. Where the multifunctional compound is modified to include bioabsorbable groups, the bioabsorbable groups may be present in an amount ranging from about 50 percent to about 95 percent of the combined weight of the multifunctional compound and bioabsorbable groups, typically from about 7 percent to about 90 percent of the combined weight of the multifunctional compound and bioabsorbable groups.

The multifunctional compound can have a weight average molecular weight ranging from about 50 to about 5000, typically from about 100 to about 3000, and typically possesses a functionality ranging from about 2 to about 6.

Methods for reacting the multifunctional compound with the functionalized diacid compound are within the purview of those skilled in the art. In some embodiments, the multifunctional compound optionally may be combined with a diisocyanate-functional compound in the presence of a catalyst such as stannous octoate at a temperature ranging from about 50° C. to about 80° C., typically from about 60° C. to about 70° C. for a period of time ranging from about 24 to about 96 hours, typically from about 48 to about 72 hours.

The resulting branched, functionalized compound may thus be of the following formula:

Z—(OCN—X—HNCOO—(R-A)$_n$-R—OOCNH—X—NCO)$_m$ wherein Z is a group derived from a multifunctional compound which optionally contains bioabsorbable groups; X is an aliphatic or aromatic group; A is a group derived from an aliphatic diacid; R can be the same or different at each occurrence and is a group derived from a dihydroxy compound; n is 1 to 10; and m is 2 to 6. The viscosity of these branched diisocyanate-functional compounds will depend on a number of factors such as the particular branching agent used, the particular diisocyanate used, the particular diacid used, the particular dihydroxy compound used and the number of repeat units present. Generally, the viscosity of these compounds may be from about 3,000 to about 300,000 Cp at 25° C. and 9.98 s$^{-1}$ shear rate, in some embodiments about 15,000 to about 100,000 Cp at 25° C. and 9.98 s$^{-1}$ shear rate and in yet other embodiments, about 30,000 to about 70,000 Cp at 25° C. and 9.98 s$^{-1}$ shear rate.

As those skilled in the art will appreciate, a mixture of compounds having various degrees of functionality will result from reacting the diisocyanate-functional compound with the multifunctional compound. For example, a single diisocyanate-functional compound may react with the multifunctional compound to provide a compound with a single isocyanate functionality; or two diisocyanate-functional compounds may react with a single multifunctional compound to provide a compound with a two isocyanate functionalities; or three diisocyanate-functional compound may react with a single multifunctional compound to provide a compound with a three isocyanate functionalities; or two multifunctional compound may react with a single diisocyanate-functional compound to provide a compound with no isocyanate functionalities. Those skilled in the art will envision other possible reaction products that may form.

It should be understood that more than one diisocyanate-functional compound can be reacted with a multifunctional compound in a single reaction. For example, aliphatic polyester macromer of the above-mentioned formula wherein n is 3 can be prepared and combined with aliphatic polyester macromer of the above-mentioned formula wherein n is 5 that had been separately prepared. The mixture of aliphatic polyester macromers can then be endcapped to provide a reactive group in a single reaction. The resulting mixture of diisocyanate-functional compounds can then be reacted with a multifunctional compound. As another example, aliphatic polyester macromer of the above-mentioned formula wherein n is 3 can be prepared and endcapped and an aliphatic polyester macromer of the above-mentioned formula wherein n is 5 can be separately prepared and endcapped. The two diisocyanate-functional compounds can then be mixed. The resulting mixture of diisocyanate-functional compounds can then be reacted with a multifunctional compound in a single reaction.

Upon administration to tissue in situ, the functionalized compounds and branched, functionalized compounds described hereinabove cross-link to form a gel matrix that serves as an excellent tissue adhesive or sealant. Normally, the cross-linking reaction is conducted at temperatures ranging from about 20° C. to about 40° C. for a period of time ranging from about fifteen seconds to about 20 minutes or more typically 1 to 10 minutes.

The compounds described hereinabove can be used alone or can be formulated into compositions. The concentrations of the components utilized to form the compositions will vary depending upon a number of factors, including the types and molecular weights of the particular components used and the desired end use application of the biocompatible composition, e.g., an adhesive or sealant. Generally, the composition may contain from about 0.5% to about 100% of the previously described functionalized polyester macromer. Where the functionalized polyester macromer has been reacted with a branching agent, the composition may contain from about 0.5 to about 10% of the branching agent by weight.

If the viscosity of the compounds of the present disclosure is deemed too high for a particular application, solutions or emulsions may be formulated that include a solvent in addition to the compounds. Suitable solvents which may be utilized include, for example, polar solvents such as water, ethanol, triethylene glycol, glymes (such as diglyme, triglyme, tetraglyme, and the like), polyethylene glycols, methoxypolyethylene glycols, dimethylformamide, dimethylacetamide, gamma-butyrolactone, N-methylpyrolidone, ketones such as methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, and the like, and mixtures thereof. In other embodiments, solvents such as tetrahydrofuran, ethyl acetate, isopropyl acetate, butyl acetate, isopropanol, butanol, acetone, mixtures thereof, and the like, may be utilized.

The amounts of solvent used will depend on a number of factors including the particular reactive compound employed and the intended end use of the composition. Generally, the solvent will be from about 1 to about 50 weight percent of the entire composition. The use of one or more solvents can produce an emulsion having a viscosity of from about 100 to about 1500 Cp. Such emulsions can advantageously be sprayed using any suitable spraying device.

Where the compound includes isocyanate functionality and the solvent contains hydroxyl groups, the solvent is advantageously mixed with the compounds immediately prior to use to avoid undesired pre-gelling.

Compositions in accordance with this disclosure may optionally include one or more catalysts. The addition of a catalyst can decrease the cure time of the compositions of the present disclosure. Catalysts which may be utilized include Lewis acids, tertiary amine catalysts, quaternary amine catalysts, and the like.

Suitable tertiary amine catalysts which may be added include, but are not limited to, triethylenediamine, N-methylmorpholine, pentamethyl diethylenetriamine, dimethylcyclohexylamine, tetramethylethylenediamine, 1-methyl-4-dimethylaminoethyl-piperazine, 3-methoxy-N-dimethylpropylamine, N-ethylmorpholine, diethylethanolamine, N-cocomorpholine, N,N-dimethyl-N',N'-dimethylisopropylpropylene diamine, N,N-diethyl-3-diethyl aminopropylamine and dimethyl-benzyl amine.

Suitable quaternary amine catalysts include, for example, lower alkyl ammonium halides and their derivatives such as hydroxy, chlorhydrin and epoxy substituted lower alkyl trimethylammonium halides such as substituted propyltrimethylammonium chlorides. Quaternary amines which may be utilized include dihydroxypropyltrimethylammonium chloride, chlorohydroxypropyltrimethylammonium chloride, and epoxypropyl-trimethylammonium chloride. Specific examples of the above compounds include 3-chloro-2-hydroxypropyl trimethyl ammonium chloride, 2,3-epoxypropyl trimethyl ammonium chloride, 3-chloro-2-hydroxypropyl trimethyl ammonium chloride, and 2,3-dihydroxypropyltrimethyl ammonium chloride.

In other embodiments, catalysts for use in the cross-linking reaction include 1,4-diazobicyclo[2.2.2]octane, stannous octoate, and the like.

The amount of catalyst employed can range from about 0.5 grams to about 50 grams per kilogram of the compound being cross-linked. In one embodiment, the amount of catalyst ranges from about 0.5 grams to about 10 grams per kilogram of the compound being cross-linked.

Water may also be added to the composition to decrease cure time. When added, water should be introduced at or near the time of use of the composition to avoid unwanted or pre-mature crosslinking. Generally, the amount of water may be from about 1 to about 50 weight percent based on the entire composition.

A variety of optional ingredients may also be added to the bioabsorbable compositions of the present disclosure, including but not limited to surfactants antimicrobial agents, colorants, preservatives, imaging agents e.g., iodine or barium sulfate, or fluorine, or medicinal agents. In some embodiments, the present compositions may optionally contain one or more bioactive agents. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the present compositions include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine or rh-lactoferrin and lactoferricin B may be included as a bioactive agent in the present compositions.

Other bioactive agents which may be included as a bioactive agent in the present compositions include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present compositions include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Naturally occurring polymers, including proteins such as collagen and derivatives of various naturally occurring polysaccharides such as glycosaminoglycans, can optionally be incorporated into the compositions the bioactive agent of the present disclosure.

A single bioactive agent may be utilized to form the present compositions or, in alternate embodiments, any combination of bioactive agents may be utilized to form the present compositions.

Due to the presence of the functionalized compounds and branched, functionalized compounds described hereinabove, the present compositions cross-link to form a gel matrix that serves as an excellent tissue adhesive or sealant. Normally, the cross-linking reaction is conducted at temperatures ranging from about 20° C. to about 40° C. for a period of time ranging from about fifteen seconds to about 20 minutes or more typically 30 seconds to 10 minutes. The exact reaction conditions for achieving cross-linking of the compositions of the present disclosure depend upon a variety of factors, including the functionality of the compound, the degree of endcapping, the degree of functionalization, the presence of a catalyst, the particular solvent, if any, present and the like.

The cross-linked compositions can be used in a medical/surgical capacity in place of, or in combination with, sutures, staples, clamps and the like. In one embodiment, the present compositions can be used to seal or adhere delicate tissue together, such as lung tissue, in place of conventional tools that may cause mechanical stress. The present compositions can also be used to seal air and/or fluid leaks in tissue as well as to prevent post-surgical adhesions and to fill voids and/or defects in tissue.

Where the bioabsorbable composition is intended for delivery of a drug or protein, the amounts of the compounds of the present disclosure can be adjusted to promote the initial retention of the drug or polymer in the bioabsorbable composition and its subsequent release. Methods and means for making such adjustments will be readily apparent to those skilled in the art.

The compositions of the present disclosure can be used for a number of different human and animal medical applications including, but not limited to, wound closure (including surgical incisions and other wounds). Adhesives may be used to bind tissue together either as a replacement of, or as a supplement to, sutures, staples, tapes and/or bandages. Use of the present compositions can eliminate or substantially reduce the number of sutures normally required during current practices, and eliminate the subsequent need for removal of staples and certain types of sutures. The compositions described herein can thus be particularly suitable for use with delicate tissues where sutures, clamps or other conventional tissue closure mechanisms may cause further tissue damage.

To effectuate the joining of two tissue edges, the two edges are approximated, and a composition of the present disclosure is applied to the two approximated edges. The composition crosslinks rapidly, generally taking less than one minute. Compositions of the present disclosure can thus be applied to the wound and allowed to set, thereby closing the wound.

While certain distinctions may be drawn between the usage of the terms "flesh" and "tissue" within the scientific community, the terms are used interchangeably herein as referring to a general substrate upon which those skilled in the art would understand the present bioabsorbable composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

The compositions described herein can also be used as sealants. When used as a sealant, a compound of the present disclosure can be used in surgery to form a bioabsorbable composition to prevent or inhibit bleeding or fluid leakage both during and after a surgical procedure. It can also be applied to prevent air leaks associated with pulmonary surgery. Compounds herein may be applied directly to the desired area in at least an amount sufficient to seal off any defect in the tissue and seal off any fluid or air movement. The compositions may also be used to prevent or control blood or other fluid leaks at suture or staple lines.

The present compositions also can be used to attach skin grafts and position tissue flaps during reconstructive surgery. Alternatively, the present compositions can be used to close tissue flaps in periodontal surgery.

Application of the compositions of the present disclosure can be done by any conventional means. These include dripping, brushing, or other direct manipulation of the compositions on the tissue surface, or spraying of the compositions onto the surface. In open surgery, application by hand, forceps or the like is contemplated. In endoscopic surgery, the compositions can be delivered through the cannula of a trocar, and spread at the site by any device known in the art.

In other embodiments, especially where a composition of the present disclosure is to be utilized as a void filler or sealant to fill a defect in an animal's body, it may be advantageous to more precisely control the conditions and extent of cross-linking. For example, it may be desirable to partially cross-link the composition prior to use to fill a void in animal tissue. In such a case composition of the present disclosure can be applied to the void or defect and allowed to set, thereby filling the void or defect.

In another embodiment, the present disclosure is directed to a method for using compounds of the present disclosure to adhere a medical device to tissue. The medical device includes an implant. Other medical devices include, but are not limited to, pacemakers, stents, shunts and the like. Generally, for adhering a device to the surface of animal tissue, a composition of the present disclosure can be applied to the device, to the tissue surface or to both. The device and tissue surface are then brought into contact with the present composition therebetween. Once the composition crosslinks and sets, the device and tissue surface are effectively adhered to each other.

The present compositions can also be used to prevent post surgical adhesions. In such an application, a composition of the present disclosure is applied and cured to form a layer on surfaces of internal tissues in order to prevent the formation of adhesions at a surgical site during the healing process.

The resulting bioabsorbable composition has a number of advantageous properties. The bioabsorbable compositions of the present disclosure are safe, possess enhanced adherence to tissue, are biodegradable, have enhanced hemostatic potential, have low cost, and are easy to prepare and use. By varying the selection of the compounds utilized to form the bioabsorbable composition, the strength and elasticity of the bioabsorbable composition can be controlled, as can the gelation time.

The compounds herein rapidly form a compliant gel matrix as the bioabsorbable composition, which insures stationary positioning of tissue edges or implanted medical devices in the desired location and lowers overall required surgical/application time. The resulting bioabsorbable composition exhibits little or no swelling upon gel matrix formation, and therefore retains the positional integrity of the aligned tissue edges and/or location of a medical device. The bioabsorbable composition forms strong cohesive bonds. It exhibits excellent mechanical performance and strength, while retaining the necessary pliability to adhere living tissue. This strength and pliability allows a degree of movement of tissue without shifting the surgical tissue edge.

In order that those skilled in the art may be better able to practice the features of the present disclosure described herein, the following examples are provided to illustrate, but not limit, the features of the present disclosure.

EXAMPLE 1

91.28 grams of PEG 600 (Sigma Aldrich, St. Louis, Mo.) were added to a clean oven dried and nitrogen cooled (dry herein) 0.5 liter single neck flask. 175 grams (196 ml) of tetrahydrofuran (THF) (J T Baker, Phillipsburg, N.J.) was added to the flask, which dissolved the PEG 600, and then 13.6 grams of anhydrous pyridine (EMD Sciences, Gibbstown, N.J.) were added to the flask. Once dissolved, the solution was added to a dry graduated addition funnel. 19.042 grams of distilled adipoyl chloride (AdCl) (98%, Sigma Aldrich, St. Louis, Mo.) were separately added to a dry one liter, two neck flask, to which 188 grams (211 ml) of THF were then added under static nitrogen.

The flask with the AdCl in THF was chilled in ice for five minutes before the PEG/pyridine/THF solution was added dropwise with stirring set at 500 rpm. The addition of the PEG/pyridine/THF solution proceeded at a rate of 90 drops/minute, with the addition being complete after about 2 hours. Mixing was allowed to continue overnight for about 16 to about 20 hours. The soluble fraction was measured in situ by infrared spectroscopy using a ReactIR™ 4000 Spectrometer (Mettler-Toledo AutoChem, Columbia, Md.); the ReactIR probe was inserted into one of the necks of the two neck flask; the background utilized was air. The spectrometer scan that was obtained confirmed the presence of PEG/AdCl at a ratio of 3:2.

The resulting material was gravity filtered through filter paper (Scheicher & Schuell #1573, ½) to remove the pyridine hydrochloride salt byproduct. The salt by-product was washed with a small amount of THF at room temperature then filtered again. The filtrate was concentrated on a ROTAVAPOR® rotary evaporator (BÜCHI Labortechnik A G, Flawil, Switzerland). Approximately ¾ of the THF was removed, after which the resulting material was precipitated in 800 ml of anhydrous ethyl ether (Reagent Grade, ACS, 99.0%, VWR International,) stirred at 400 rpm. The mixture was stirred for thirty minutes. The stirring was stopped and the mixture allowed to separate after which the supernatant was and the precipitate transferred to a jar. The product, PEG/adipate at a 3:2 ratio, sometimes referred to herein as dPEG, was vacuum dried overnight.

An additional PEG/adipate was produced using the method described above, but at a ratio of 2:1 (PEG:adipate).

EXAMPLE 2

Isocyanate endcapping of PEG adipate. A dry 500 ml three neck flask was outfitted with a mechanical stir assembly and dry condenser. The apparatus were setup in a dry room at 2% relative humidity. 57.0 grams of the PEG/adipate produced above in Example 1 was transferred to the flask. 39 grams of toluene diisocyanate (TDI) (technical grade 80%, Sigma Aldrich, St. Louis, Mo.) was added to the flask and the resulting mixture was stirred at 110 rpm and heated to 65° C. while under static nitrogen over night (for 16 to 20 hours). The following day, the temperature was reduced to 60° C., then approximately 150 ml of petroleum ether (ACS Reagent, Sigma Aldrich, St. Louis, Mo.) was added and mixed at 250 rpm for 20 to 30 minutes. The flask was then removed from the heat and the supernatant was decanted. The above process was repeated three times. On the fourth repeat of the process, the solvent was added and stirred for approximately 30 seconds, at which time the supernatant was decanted and the precipitate transferred to a jar (a total of about 60 grams). The material was then vacuum dried at room temperature.

Viscosity was calculated using a Brookfield DV III cone and plate viscosmeter and Rheocalc V2.5 software from Brookfield Engineering Labs, Middleboro, Mass. NCO content was determined by titration on a TitroLine Alpha Autotitrator manufactured by Schott Geräte GmbH, Mainz, Germany using a modification of ASTM D 2572-91. The average NCO content of the material pre-extraction was about 17.9%; the average NCO content of the material post-extraction was about 4.2%. The presence of the NCO endcapped PEG/adipate was confirmed by FTIR and NMR.

EXAMPLE 3

A degradable branching agent was prepared. To a clean and dry 250 ml three neck flask outfitted with a mechanical stir assembly was added 0.011 grams of stannous octoate (Brand Nu Labs, Meriden Conn.), 8.0 grams of trimethylol propane (TMP) (97% Sigma Aldrich, St. Louis, Mo.), and 30.66 grams of p-dioxanone (US Surgical, Norwalk, Conn.). The mixture was mixed at 50 rpm and placed under static nitrogen overnight. The next morning the reaction mixture was a liquid at 24° C. The reaction mixture was heated to approximately 110° C. for approximately 6 hours, after which 7.0 grams of glycolide (US Surgical, Norwalk, Conn.) was added and temperature was gradually increased to 160° C. After one hour at 160° C., the temperature was reduced to 125° C. for approximately one hour and 15 minutes, after which time the reaction mixture was transferred to a jar and left overnight (about 15 hours).

40 grams of the reaction mixture was then added to a 200 ml single neck flask which, in turn, was heated to 75° C. under vacuum for 24 hours and stirred a rate of 250 rpm. About 26 hours later, the reaction mixture was transferred to a 200 ml single neck flask, and refluxed in ethyl ether while stirring at 200 rpm for 20 minutes. The supernatant was decanted and the refluxing procedure repeated two times to remove residual stannous octoate. The resulting material, a TMP/dioxanone/glycolide branching agent, was transferred to a jar and allowed to dry.

EXAMPLE 4

The NCO endcapped PEG/adipate of Example 2 was combined with the branching agent of Example 3. 16.59 grams of the NCO endcapped PEG/adipate of Example 2, having an NCO content of 4.2% and a molecular weight of about 3900, was added to a 250 ml three neck flask with a mechanical stir assembly. 0.857 grams of the TMP/dioxanone/glycolide branching agent produced in Example 3 was added to the flask, which was heated to 65° C. while stirring at 50 rpm under static nitrogen. The reaction was allowed to proceed for about 65 hours, at which point the material was transferred to a beaker. The beaker was vacuum dried for one hour then the material was tested for its isocyanate content by titration and found to have an NCO content of about 2.6%.

EXAMPLE 5

Adhesives utilizing NCO-terminated PEG/adipate prepared according to the procedures set forth above in Example 2 and TMP/dioxanone/glycolide branching agents prepared according to the procedures set forth above in Example 3 were obtained following the procedures described above in Example 4. Additional adhesives were prepared using TMP as a branching agent instead of the branching agents of Example 3. The adhesives that were prepared and their components are summarized below in Table 1. The viscosity was obtained as per the procedures set forth in Example 2 above and NCO content was determined as per the procedures set forth in Example 4 above.

TABLE 1

| ADHESIVE | BASE MATERIAL | BRANCHING AGENT | ADHESIVE VISCOSITY, cP | NCO % |
|---|---|---|---|---|
| A | dPEG (3:2) | TMP | 127,000 | 3.5 |
| B | dPEG (3:2) | TMP | 42,000 | 2.8 |
| C | dPEG (3:2) | dTMP | 56,000 | 2.6 |
| D | dPEG (3:2) | dTMP | 26,000 | 3.6 |
| E | dPEG (3:2) | dTMP | 59,000 | 3.0 |
| F | dPEG (2:1) | TMP | 70,000 | 3.8 |

The Base Material for Adhesives A-E, dPEG was a PEG600 chain extended with adipoyl chloride at a ratio of 3:2 (PEG600:adipoyl chloride) and TDI; Adhesive F was a PEG600 chain extended with adipoyl chloride at a ratio of 2:1 (PEG600:adipoyl chloride) and TDI. TMP = trimethylolpropane (Aldrich Lot# 10628CA) dTMP = TMP and dioxanone and glycolide. 0.15 grams Bis(hydroxymethyl) propionic acid (BmhP) was added during the branching step in the preparation of Adhesive A.

EXAMPLE 6

Burst Testing

Staples, adhesives produced above in Example 5, and combinations thereof were subjected to a burst test. The burst test utilized a 25 mm end-to-end anastomosis device (from U.S. Surgical, Norwalk, Conn.) and a test sample of fresh canine colon to test the ability of the adhesives of Example 5 to supplement or replace staples inserted with the end-to-end anastomosis device.

Briefly, the procedure for the burst test was as follows. The anastomotic site of interest was first isolated and a sample was excised. Sufficient tissue was maintained proximal and distal of the staple line (approximately 4 cm each side) to allow the sample to be properly fixtured in a hemostatic clamp. A hypodermic needle was inserted from a syringe pump equipped with a pressure transducer in line into the distal end of the sample and positioned in the clamp with the needle oriented towards the handle of the clamp so that the staple line was centered. The sample was then placed in a triangular test tank, and a sodium fluorescein fluid line was attached to the hypodermic needle. Sodium fluorescein solution was injected into the sample at a rate of 5 cc/min until failure was observed and peak pressure was noted.

Staples only. The anastomosis was performed as per Steichen, et al., ("Mechanical Sutures in Operations on the Small & Large Intestine & Rectum," Woodbury, Conn.: Ciné-Med, Inc. (2004):72-76), using a 25 mm PPCEEA stapler. The burst pressure test was performed as described above. The burst pressure for the anastomosis sealed only with staples was 0.7 psi-1.3 psi, n=10.

Staples and Adhesive C. The anastomosis was performed as per Steichen et al. using a 25 mm PPCEEA stapler, except that after docking the anvil, but before firing the staples, a bead of Adhesive C (~0.2 mL) was applied to the tissue on the instrument side approximately between the two rows of staples. After firing, the instrument was removed and the adhesive was allowed to cure for five minutes before performing the burst test. The burst pressure for the anastomosis sealed with the staples and Adhesive C was 1.49 psi-2.1 psi, n=2.

Compromised Anastomosis. Three staples were removed from a 25 mm PPCEEA stapler, two adjacent to the edge of the material, and a third adjacent thereto but closer to the center of the material. The anastomosis was performed as per Steichen et al. using the 25 mm PPCEEA stapler, making sure the compromised portion of the anastomosis was on the anti-mesenteric side of the bowel. The burst pressure for the compromised anastomosis was 0.3 psi, n=10.

Compromised Anastomosis and Adhesive C or Adhesive E. Three staples were removed from a 25 mm PPCEEA stapler, two adjacent to the edge of the material, and a third adjacent thereto but closer to the center of the material. The anastomosis was performed as per Steichen et al. using the 25 mm PPCEEA stapler, except that after docking the anvil, but before firing the staples, a bead of Adhesive C (~0.2 mL) was applied to the tissue on the instrument side approximately between the two rows of staples. As above, the compromised portion of the anastomosis was on the anti-mesenteric side of the bowel. The instrument was removed and the adhesive was allowed to cure for five minutes before performing the burst test. The burst pressure of Adhesive C in combination with some, but not all, of the staples was 2.1-5.9 psi, n=2.

The same procedure was performed to form a compromised anastomosis, except Adhesive E was utilized instead of Adhesive C. The burst pressure of Adhesive E was 1.12 psi, n=1.

Adhesive E alone with no staples. All staples were removed from a 25 mm PPCEEA. The anastomosis was then performed according to Steichen et al., but before firing the instrument, a bead of Adhesive E (~0.2 mL) was applied to the tissue on the instrument side approximately between where the two rows of staples would be. Once the instrument was fired, it was opened slightly to reduce the compression on the tissue but it was not opened completely. This was done to keep the ends of the anastomosis together during the five minutes cure time of the adhesive. After five minutes of curing, the anastomosis was tested using the burst test. The burst pressure of Adhesive E was 1.48 psi, n=1.

EXAMPLE 7

Mesh Pull-Off Testing

The purpose of this example was to mimic hernia repair using a polypropylene mesh with an adhesive. Approximately 0.1 ml of adhesive was placed onto a 16 mm diameter circular piece of mesh with a suture loop through it. The mesh was then placed onto the peritoneum and immediately treated with one drop of saline. After several minutes, the mesh was pulled away from the tissue and the tensile force required to remove the mesh was measured using a Model BG10 premium series force gauge manufactured by Mark-10, Copiague, N.Y. and then recorded. The adhesives utilized, the cure time, pull force (in grams), and observations regarding these tests are set forth below in Table 2.

TABLE 2

| Adhesive | Substrate | Cure Time min | Pull Force (grams) | Observations |
|---|---|---|---|---|
| C | Peritoneum | 7 | 1374 | — |
| C + 10% wt/wt NaHCO$_3$ | Peritoneum | 7 | 920 | — |
| C | Peritoneum | 2 + 2.5 | 520 | Mesh was pulled off at 2 min, placed back down in the same place, and pulled again after 2.5 more minutes |
| C | Peritoneum | 5 | 690 | Fascia began to separate from muscle |

TABLE 2-continued

| Adhesive | Substrate | Cure Time min | Pull Force (grams) | Observations |
|---|---|---|---|---|
| C | Peritoneum | 5 | 726 | layer while pulling Saline was applied once per minute after initial application |
| C | Peritoneum | 4 | 700 | — |

EXAMPLE 8

Abdominal Aorta Graft

An end-to-side anastomosis was created on the abdominal aorta using an expanded PTFE tubular graft. The graft was sewn on using a 6 pass, interrupted suture. 0.2 mL of Adhesive E was applied through a 16 gauge cannula as a bead around the anastomosis. The adhesive was flushed with saline and let cure for 6 minutes before unclamping the aorta and checking for leaks.

Once the adhesive had been allowed to cure for 6 minutes, the clamps on the aorta were removed to allow complete blood flow past the anastomosis. There were no apparent leaks immediately after the clamps were removed, and even after 10 minutes and manipulation of the graft, there were still no leaks. No bleeding at all was observed through the anastomosis at any time.

EXAMPLE 9

In Vitro Strength Loss Test

Two rigid foam test blocks were soaked in water prior to application of the adhesive for testing. 0.05 ml of Adhesive B was applied to one testing block using a syringe, the $2^{nd}$ test block mated to the first where the adhesive had been applied, and a 20 gram weight was balanced on top of the construct for 5 minutes. After 1 hour, samples were placed into a glass jar filled with water for 24 hours. The samples were tested for tensile properties using an MTS Sintech 1/G instrument. The first sample was tested by mounting the sample onto the Sintech1/G using screw action grips and then loaded to failure at 2 in/min to obtain time zero data. The remaining samples were submerged in Sorrenson's buffer and placed into a 37° C. bath for varying time periods of 1 week, two weeks, and four weeks before testing. Tensile data results after 1 week, 2 weeks and 4 weeks in the in vitro bath were obtained as described above with the MTS Sintech 1/G instrument and compared with the time zero data to evaluate strength loss.

Figure 1:
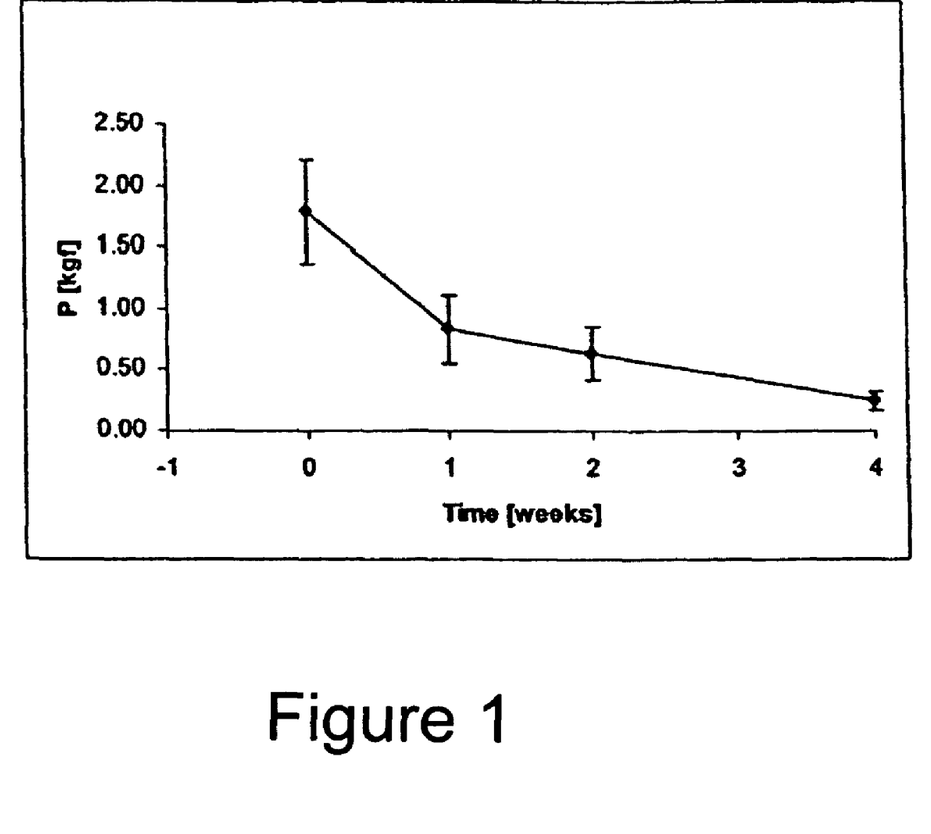
FIG. 1 is a graph depicting the strength loss profile of an adhesive of the present disclosure from administration (day 0) through week 4 post-administration.

The peak loads at failure were recorded for each sample and the strength loss profile is set forth below in Table 3 and accompanying FIG. 1.

TABLE 3

| Time | Peak Load [kgf] | St. Dev. | % loss |
|---|---|---|---|
| 0 | 1.79 | 0.42 | |
| 1 week | 0.84 | 0.27 | 53.1 |
| 2 weeks | 0.64 | 0.22 | 23.7 |
| 4 weeks | 0.24 | 0.08 | 61.7 |
| | Total loss | | 86.3 |

The material exhibited strength loss after each time period, with the greatest loss occurring after the first week. There was an initial strength of 1.79 kg with an 86% loss in strength after 4 weeks. FIG. 1 is a graph depicting the strength loss profile of the adhesive from administration (day 0) through week 4 post-administration. If strength loss continued along the same trend observed through week 4 (see FIG. 1), total loss in strength could be expected after about 5.24 weeks post-administration.

EXAMPLE 10

Cytotoxicity Test

The cytotoxicities of Adhesive A and Adhesive F were tested. 1.5 mL of each adhesive was injected directly into a 20 mL MEM solution (Modified Eagle Medium, from Invitrogen Corporation). The cytotoxicity was tested following ISO 10993-5 guidelines. Briefly, the results of the tests are provided on a 5 scale ranking system in which a score of 0, 1, 2, 3, or 4 is obtained. A score of 0 indicates no toxic reaction was observed and a score of 4 indicates a strong toxic reaction was observed. A score of 0, 1, or 2, is considered a non-toxic score, a score of 3 is considered weakly to moderately toxic, and a score of 4 is considered strongly toxic. Scores of 0, 1, or 2 are considered passing scores, that is, the samples do not produce a cytotoxic response.

Adhesive F had a cytotoxicity grade 2, while Adhesive A in combination with BmhP had a cytotoxicity grade 0.

EXAMPLE 11

Lap Shear Test

Adhesives C, D, and E, were each subjected to a lap shear test. Briefly, room temperature porcine stomach tissue was cut into 15×45 mm pieces using a punch. The tissue was rinsed with saline and blotted to remove excess moisture. 0.1 mL of adhesive was then applied to the end of one of the tissue pieces. The adhesive was spread around to cover an area 15×15 mm at the end of the tissue piece. Another tissue piece was placed on top of the area covered by the adhesive. A 20 gram weight was placed on top of the adhered area for 30 seconds. The weight was removed and the adhesive was allowed to cure for 4.5 minutes more, for a total of 5 minutes cure time. Three separate tissue constructs were prepared, one for each Adhesive C, D and E.

For each tissue construct, the free end of one of the tissue pieces was placed into a grounding clamp, while the free end of the other tissue piece was placed into a second clamp mounted on a counter. A Model BG10 premium series force gauge was attached to the grounding clamp and the force required to pull the pieces apart was recorded.

Adhesive C demonstrated a lap shear of 1100 grams; Adhesive D demonstrated a lap shear of 1262 grams, and Adhesive E demonstrated a lap shear of 1322 grams.

It will be understood that various modifications may be made to the embodiments disclosed herein. For example, the diisocyanate functionalized aliphatic polyester macromer can be used to prepare polyurethanes and used for applications other than adhesives or sealants. As another example, the branched diisocyanate functionalized aliphatic polyester macromer can be cross-linked and molded into solid articles useful in a variety of applications, including but not limited to solid, biodegradable implants. Therefore the above description should not be construed as limiting, but merely as exemplifications of preferred embodiments. Those skilled in the art will envision other modifications within the scope and spirit of the claims appended hereto.

What is claimed is:

1. A branched isocyanate functional compound prepared by reacting at least two different aliphatic polyester macromers of the formula HO—(R-A)$_n$-R—OH wherein A is an acid selected from the group consisting of sebacic acid, azelaic acid, suberic acid, pimelic acid, adipic acid, glutaric acid, succinic acid, malonic acid, oxalic acid and combinations thereof; R can be the same or different at each occurrence and comprises a dihydroxy compound selected from the group consisting of polyethylene oxides, polypropylene oxides, block or random copolymers of polyethylene oxides and polypropylene oxides, and polyethylene glycols having a molecular weight less than 1,000; and n is 1 to 10, with at least one diisocyanate in a single reaction to provide a mixture of diisocyanate-endcapped macromers; and reacting the mixture of diisocyanate-endcapped macromers with a multifunctional compound in a single reaction to provide a mixture of branched isocyanate functional compounds.

2. A composition comprising a branched isocyanate functional compound in accordance with claim 1.

* * * * *